United States Patent [19]

Tanaka et al.

[11] Patent Number: 4,873,342

[45] Date of Patent: Oct. 10, 1989

[54] DIPEPTIDE DERIVATIVE AND SYNTHESIS AND USE THEREOF

[75] Inventors: Takaharu Tanaka; Masayuki Saitoh; Naoki Higuchi; Masaki Hashimoto, all of Osaka, Japan

[73] Assignee: Suntory Limited, Osaka, Japan

[21] Appl. No.: 852,710

[22] Filed: Apr. 16, 1986

[30] Foreign Application Priority Data

Apr. 16, 1985 [JP] Japan .................................. 60-80871
Dec. 23, 1985 [JP] Japan ................................ 60-290237

[51] Int. Cl.$^4$ ..................... C07D 207/00; A61K 31/40
[52] U.S. Cl. ..................................... 548/518; 540/480; 540/602; 546/208; 548/533; 548/540
[58] Field of Search ..................... 548/518, 533, 540; 546/208; 540/480, 602; 514/210, 212, 422, 423

[56] References Cited

U.S. PATENT DOCUMENTS 4,374,829 2/1983 Harris et al. .......................... 424/177
4,743,616 5/1988 Tanaka et al. ........................ 514/423

FOREIGN PATENT DOCUMENTS 172458 7/1985 European Pat. Off. .
154353 9/1985 European Pat. Off. ............. 514/423
60-172929 9/1985 Japan .
60-188317 9/1985 Japan .

OTHER PUBLICATIONS

Galardy et al., Chem. Abstracts, 98:13958bn, (1983).
Greenlee et al., Chem Abstracts, 102:132451g, (1985).
Weller et al., Chem. Abstracts, 102:91911m, (1985).
Wilchek et al., Chem. Abstracts, 63:13407b, (1965).
Patchett et al., Nature, vol. 28, 280, (1980).
McOmie, ed., Protective Groups in Organic Chemistry, Plenum Press, (1973), p. 55.
Biochemistry, vol. 22, No. 8, Apr. 12, 1983, pp. 1990–1995.
English language version of the Proceedings of the 1984 Annual Meeting of "The Agricultural Chemical Society of Japan", pp. 752–754.
S. Wilk and M. Orlowski, Journal of Neurochemistry, vol. 41, No. 1, 1983.
Agric. Biol. Chem., 42(12), 2417–2419, 1978.

*Primary Examiner*—Anton H. Sotto
*Assistant Examiner*—Frederick F. Tsung
*Attorney, Agent, or Firm*—Cushman Darby & Cushman

[57] ABSTRACT

A novel depeptide derivative which exhibits inhibitory activity against prolyl endopeptidase and is effective for preventing and curing amnesia is disclosed. A process for chemical synthesis of such a derivative, as well as its use, is also disclosed.

2 Claims, No Drawings

DIPEPTIDE DERIVATIVE AND SYNTHESIS AND USE THEREOF

BACKGROUND OF THE INVENTION

The present invention relates to a novel dipeptide derivative that exhibits enzyme inhibiting activity against prolyl endopeptidase (EC, 3. 4. 21. 26).

More particularly, the compounds of the invention not only exhibit enzyme inhibiting activities against prolyl endopeptidase, but also are effective for the improvement and remedy of symptoms caused by an organic disorder in the brain.

The present invention also relates to the synthesis and use of such a derivative.

The term "organic disorder in the brain" here means various symptoms caused by ischemic disorders such as sequela of cerebral infarction, sequela of cerebral hemorrhage and sequela of cerebral arteriosclerosis, and various organic disorders cuased by presbyophrenia, presenile dementia, amnesia, sequela of external wounds of the head, and sequela of cerebral operation.

Prolyl endopeptidase is known to inactivate neurotransmitters such as Substance P, thyrotropin-releasing hormone (TRH) and neurotensin or vasopressin speculatively associated with memory. Tsuru and Yoshimoto of the Department of Pharmaceutical Sciences, Nagasaki University, found that compounds capable of inhibiting the prolyl endopeptidase activity were effective for preventing experimental amnesia caused in rats by scopolamine, and inferred that prolyl endopeptidase inhibitors have some relation to the fixation of memory. This suggests the potential use of prolyl endopeptidase activity inhibitors as anti-amnesic agents for preventing and curing amnesia.

Actually a novel dipeptide derivative according to the present invention which is represented by the formula (1) as shown later was confirmed to be effective as an anti-amnesic agent by animal experiments.

A brain cell retains an intracellular environment completely different from the surrounding envoironment (extracellular liquid) and lives while maintaining this difference, which requires energy to be continually produced and supplied to the cell. Most of the energy necessary for nerve cells of the brain is supplied by oxygen and glucose which are constantly supplied from the blood, since these energy sources are not stored in the brain.

If there is a disorder in the brain, and the supply of oxygen and glucose is interrupted, then energy metabolic disorders will sequentially progress and the cells will lose their functions after a time, finally causing organic collapse, and failure of normal functions.

The prevent this, brain blood vessels themselves have developed mechanisms for controlling the bloodstream so as to safely supply the energy sources for the brain tissue and maintain the external environment of the cranial nerve cells such as to be constant.

When disorders or a blood vessel in the brain are internally treated, various kinds of brain circulation improving agents, brain vasolidators, brain metabolism improving agents and the like are used. In the present state of the art, however, these agents can improve subjective symptoms but can hardly improve the symptoms of nerves.

The present inventors found compounds having anti-prolyl endopeptidase activity, and disclosed them in Japanese Patent Laid-Open No. 37764/1986. Tsuru et al. also discloses compounds having said activity in Japanese Patent Laid-Open No. 188317/1985.

SUMMARY OF THE INVENTION

The present inventors have made various studies to find a compound having anti-prolyl endopeptidase activity and anti-amnesic activity which are considered associated with the improvement and remedy of symptoms caused by various disorders in the brain described above. Further, to find a novel compound of sufficiently low toxicity, they synthesized compounds which have structures similar to natural substances by combination of fatty acids with amino acids or peptide compounds which are highly safe as natural compounds.

As a result, it has been found that a novel compound according to the present invention which is represented by the general formula (1) has anti-prolyl endopeptidase activity. This compound exhibits the strongest anti-prolyl endopeptitase activity among the anti-prolyl endopeptidase compounds heretofore discovered (Tadashi yoshimoto, Agr. Biol. chem. Assoc. (Japan), Synopses of Lectures, pp 752 to 754, (1983), and Japanese Patent Application No. 160994/1984, filed on July 31, 1984).

The present inventors have also found that a novel dipeptide derivative represented by the general formula (1) having anti-prolyl endopeptidase activity has anti-amnesic effects on laboratory animals.

The present invention has been accomplished on the basis of these findings.

A novel dipeptide derivative according to the present invention which is represented by the formula (1) is effective for the improvement and remedy of mental symptoms caused by organic disorders in the brain and, especially, for improvement and remedy of amnesia.

The compounds according to the present invention represented by the formula (1) differ greatly from the known piracetam derivatives based anti-amnesic agents in that the former contains a proline group. Because of this feature, the compounds of the formula (1) present extremely low toxicity levels in organisms.

DETAILED DESCRIPTION OF THE INVENTION

The novel dipeptide derivatives of the present invention are represented by the formula (1):

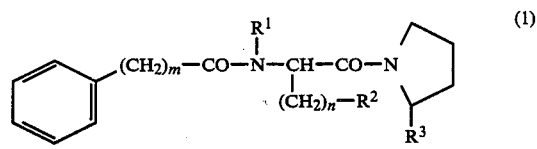

(wherein m is an integer of 1 to 8; n is 0 or an integer of 1 to 6; $R^1$ is hydrogen atom; $R^2$ is hydrogen atom, a branched alkyl group having 3 to 5 carbon atoms, phenyl group, hydroxyphenyl group or methylthio group, or $R^1$ and $R^2$ together represent a single bond between carbon atom and nitgogen atom; and $R^3$ is a lower alkyl ester group, hydroxymethyl group or formyl group; provided that when n is 0, $R^2$ represents one of the above-described groups except hydrogen atom).

When $R^2$ is the branched alkyl group, it can be, for examle, isopropyl, sec-butyl, tert-butyl, 1-methylbutyl, 1-ethylpropyl or 1,1-dimethylpropyl, among which isopropyl is particularly preferred.

When $R^3$ is a lower alkyl ester, preferred examles are methoxycarbonyl group, ethoxycarbonyl group, propoxycarbonyl group, isopropoxycarbonyl group, butoxycarbonyl group, sec-butoxycarbonyl group and t-butoxycarbonyl group.

One preferred group among the compounds of the present invention of the formula (1) is expressed by the formula:

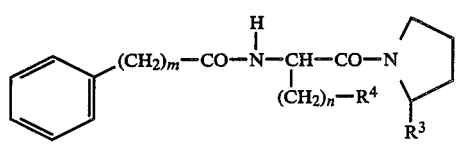

(whrein, m, n and $R^3$ have the same meanings as given above; and $R^4$ is hydrogen atom, a branched alkyl group having 3 to 5 carbon atoms, phenyl group, hydroxyphenyl group or methylthio group, provided that when n is 0, $R^4$ represents one of said groups except hydrogen atom).

In this embodiment, $R^4$ when n is 0 is preferably a branched alkyl group having 3 to 5 carbon atoms.

Another preferred group of compounds of the invention are expressed by the formula:

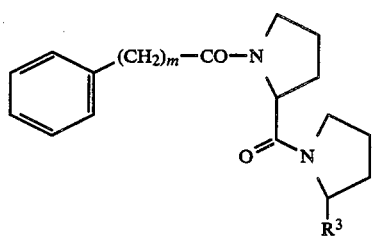

(wherein m and $R^3$ have the same meanings as given above).

The following compounds of the formula (1) are particularly preferred because of their high anti-prolyl endopeptidase activities. The following compounds will sometimes be referred to by the respective numbers indicated in the parentheses shown hereinunder.

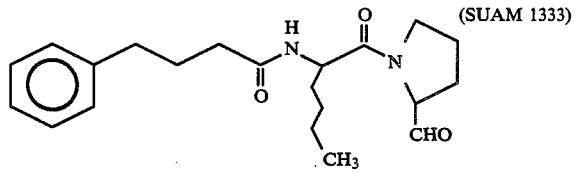
(SUAM 1333)

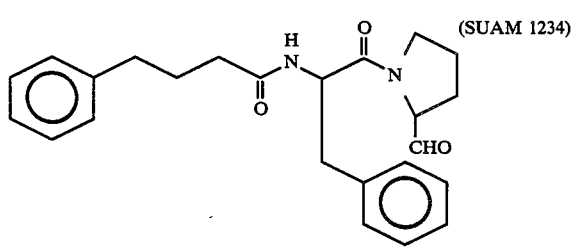
(SUAM 1234)

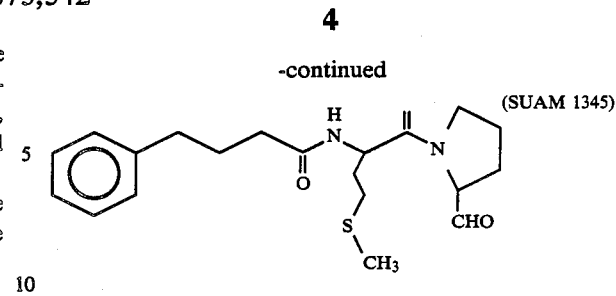
(SUAM 1345)

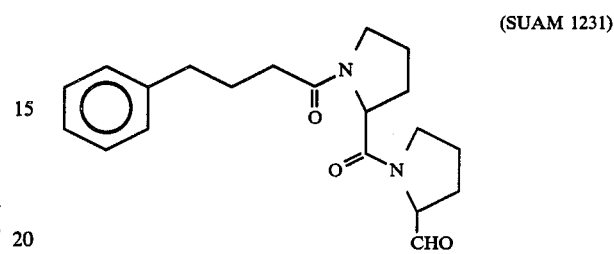
(SUAM 1231)

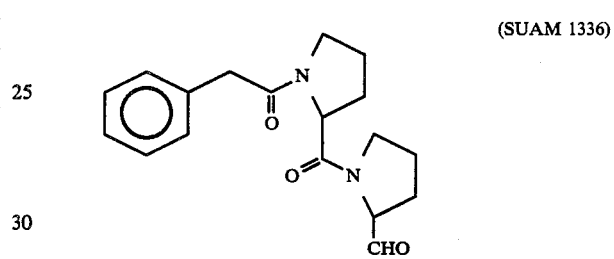
(SUAM 1336)

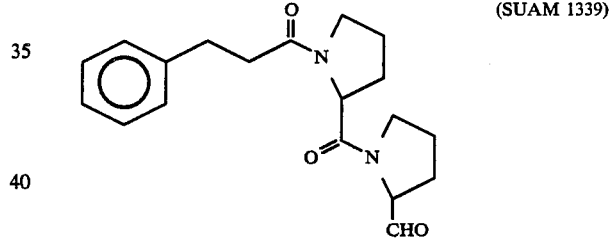
(SUAM 1339)

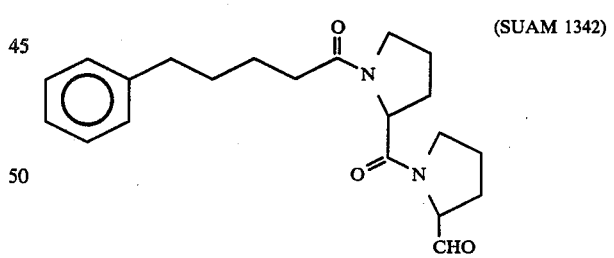
(SUAM 1342)

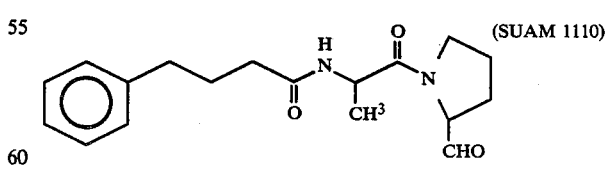
(SUAM 1110)

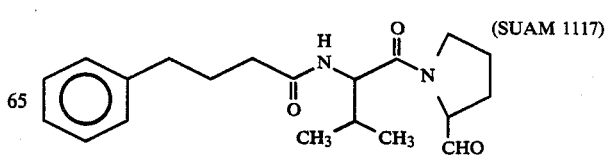
(SUAM 1117)

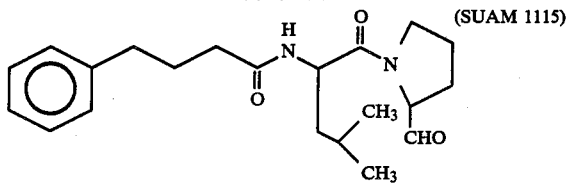 (SUAM 1115)

The compounds according to the present invention are prepared by a general peptide synthesis method, but they are more conveniently synthesized by a method according to the present invention which will be explained in the following.

Explanation of the abbreviations
Z: benzyloxycarbonyl group
Boc: tert-butyloxycarbonyl group
Pro: proline residue

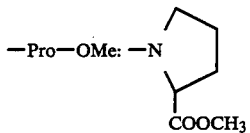

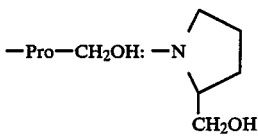

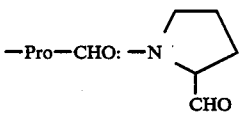

Ala: alanine residue
Val: valine residue
Leu: luecine residue
norLue: norleucine residue
Phe: phenylalanine residue
Met: methionine residue
OMe: methylester residue
WSCD: N—ethyl-N',N'—dimethylaminopropyl carbodiimide
TEA: triethylamine The compounds of the formula (1) of the present invention may be synthesized by the following procedures: (1) If the compounds have the formula (1a) wherein $R^3$ in formula (1) is a lower alkyl ester group of —COOB:

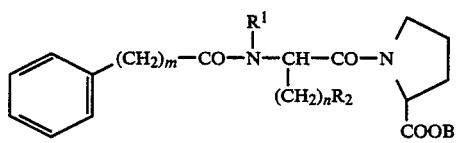 (1a)

(wherein m, n, $R^1$ and $R^2$, respectively, represent the same meanings as in the formula (1), and B represents a lower alkyl group), they may be prepared by reacting dipeptide represented by the formula (2):

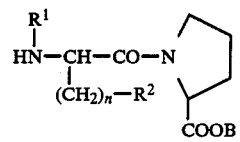 (2)

(wherein n, $R^1$, $R^2$ and B, respectively, represent the same meanings as in the formula (1a)) and carboxylic acid, acid halide or acid anhydride represented by the formula (3) in the presence of a base:

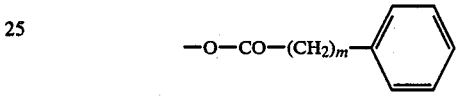 (3)

(wherein m represents the same meaning as in the formula (1)), and A represetns hydroxyl group, a halogen atom, or the following group

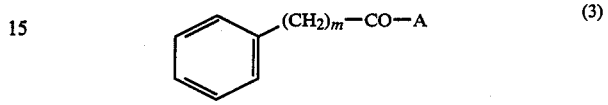

(wherein m represents the same meaning as the above).

This synthesis utilized the conventional acylating reaction of an amino group, and reagents such as a base differ depending upon which of carboxylic acid, acid halide and acid anhydride is used as the starting compound. For example, if acid halide is used, trialkylamine such as triethylamine is preferable as a base, but the aqueous solution of alkali metal hydroxide, alkalie metal carbonate or the like may be used.

When acid anhydride is used, the above-described aqueous solution of alkali metal hydroxide, e.g., sodium hydroxide and potassium hydroxide, or alkali metal carbonate such as sodium carbonate and potassium carbonate is used as a base.

When carboxylic acid is used, a condensing agent such as WSCD and dicyclohexyl carbodiimide is used in an organic solvent which is inert in the reaction.

(2) If the compounds have the formula (1b);

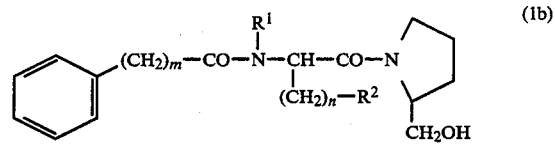 (1b)

(wherein m, n, $R^1$ and $R^2$ are the same as above), they are readily obtained by treating the compound (1a) with a reducing agent. For example, an alcohol form (1b) is obtained at a high yield by adding methanol dropwise to a suspension of the compound of the formula (1a) and sodium borohydride in tertiary butyl alcohol or tetrahydrofuran.

An alcohol form (1b) is also obtained by adding a reducing agent such as sodium borohydride, lithium borohydride, zinc borohydride, and potassium borohydride to the alcohol solution of the compound of the formula (1a).

(3) The prolinal derivative having the formula (1c):

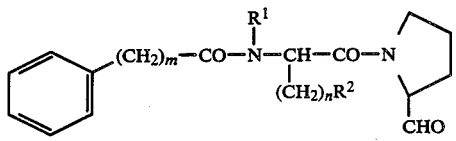

(wherein m, n, $R^1$ and $R^2$ are the same as above) is obtained by treating the compound of the formula (1b) with an oxidizing agent in an organic solvent.

The solvent used in this reaction may be anything that does not participate in the reaction, but dimethyl sulfoxide is the most preferable. As an oxydizing agent, a complex of sulfur trioxide-pyridine complex, dimethyl sulfoxide, dimethyl sulfoxide-dicyclohexyl carboimide-phosphoric acid, silver oxide and manganese dioxide may be mentioned.

When the effects of these compounds for preventing decomposition of Z-glycyl-prolyl-$\beta$-naphtylamide by prolyl endopeptidase were examined, they exhibited very high anti-prolyl endopeptidase activities as will be shown in the later-described example 4, and no inhibitory activity to proteinases such as papain, bromelain, trypsin, chymotrypsin, thermolysin and pepsin.

These compounds obtained in this way are novel and have anti-amnesic effects.

The present invention will be explained in more detail with reference to the examples.

PREPARATION

(a) H—Phe—Pro—OMe

Z—Phe—OH (1 equivalent), H—Pro—OMe hydrochloride (1 equivalent) and TEA (1 equivalent) were dissolved in dry methylene chloride, and WSCD (1 equivalent) was added dropwide under cooling with ice. After being stirred for 20 hours at room temperature, the reaction mixture was washed successively with 1N HCl, water, saturated aqueous sodium bicarbonate, water and brine, and was dried over anhydrous magnesium sulfate. The solvent was distilled off under vacuum, and the resulting residue was purified by column chromatography on silica gel. Z—Phe—Pro—OMe (1 equivalent) obtained was dissolved in ethanol (1 equivalent) and boron trifluoride etherate complex (1 equivalent) and palladium on carbon (trace) were added to remove the Z group by catalytic reduction in an atmosphere of hydrogen. The solvent was distilled off under vacuum to obtain the end compound.

In place of Z—Phe—OH, (a) Z—Met—OH, (b) Z—norLeu—OH, (c) Z—Ala—OH, (d) Z—Val—OH, and (e) Z—Leu—OH were used as the starting compounds and treated by the procedures described above to obtain (a') H—Met—Pro—OMe, (b') H—norLeu—Pr—OMe, (c') H—Ala—Pro—OMe, (d') H—Val—Pro—OMe and (e') H—Leu—Pro—OMe, respectively. All of these compounds were in the form of an oil.

(b) H—Pro—Pro—OMe

Z—Pro—OH (1 equivalent), H—Pro—OMe hydrochloride (1 equivalent) and TEA (1 equivalent) were dissolved in dry methylene chloride, and WSCD (1 equivalent) was added dropwise under cooling with ice. After being stirred for 20 hours at room temperature, the reaction mixture was washed successively with 1N HCl, water, aqueous sodium bicarbonate, water and brine, and was dried over anhydrous magnesium sulfate. The solvent was distilled off under vacuum, and the resulting residue was purified by column chromatography on silica gel. The Z—Pro—Pro—OMe obtained was dissolved (1 equivalent) in ethanol, and boron trifluoride etherate complex (1 equivalent) and palladium on carbon (trace) were added to remove the Z group by catalytic reduction in an atmosphere of hydrogen. The solvent was distilled off under vacuum to obtain the end compound as an oil.

EXAMPLE 1

(a) N—(4-phenyl)butanoyl—Phe—Pro—OMe (SUAM 1232)

H—Phe—Pro—OMe (1 equivalent) and TEA (1 equivalent) were dissolved in dry tetrahydrofuran, and 4-phenylbutanoyl chloride (1 equivalent) was added dropwise under cooling with ice. The mixture was stirred for 6 hours at room temperature, and the hydrochloride of TEA separated out was removed by filtration. The solvent was distilled off under vacuum and the resulting residue was dissolved in a small amount of ether. The ethereal solution was washed successively with 1N HCl, brine, saturated aqueous sodium bicarbonate and brine, and thereafter was dried over anhydrous magnesium sulfate. The solvent was removed under vacuum and the residue was purified by column chromatography on silica gel to obtain the required compound (an oily compound).

In place of H—Phe—Pro—OMe, (a) H—Met—Pro—OMe, (b) H—norLeu—Pro—OMe, (c) H—Ala—Pro—OMe, (d) H—Val—Pro—OMe, and (e) H—Leu—Pro—OMe were used as the starting compounds and treated by the procedures described above to obtain (a') N—(4-phenyl)butanoyl—Met—pro—OMe (SUAM 1343), (b') N—(4-phenyl)-butanoyl—norLeu—Pro—OMe (SUAM 1235), (c') N—(4-phenyl)butanoyl—Ala—Pro—OMe (SUAM 1098), (d') N—(4-phenyl)butanoyl—Val—Pro—OMe (SUAM 1112) and (e') N—(4-pehnyl)butanoyl—Leu—Pro—OMe (SUAM 1113), respectively. All of these compounds were oily.

(b) N—(4-phenyl)butanoyl—Pro—Pro—OMe (SUAM 1229)

H—Pro—Pro—OMe (1 equivalent) and TEA (1 equivalent) were dissolved in dry tetrahydrofuran, and 4-pehnylbutanoyl chloride (1 equivalent) was added dropwise under cooling with ice. The mixture were stirred for 6 hours at room temperature, and the hydrochloride of TEA separeted out was removed by filtration. The solvent was distilled off under vacuum. The resulting residue was dissolved in a small amount of ether, was washed successively with 1N HCl, brine, saturated aqueous sodium bicarbonate and brine, and thereafter was dried over anhydrous magnesium sulfate. After being condensed under a reduced pressure, the remaining product was purified by column chromatography on silica gel to obtain the required compound (an oily compound).

In place of 4-phenylbutanoyl chloride, (a) 2-phenylacetyl chloride, (b) 3-phenylpropionyl chloride and (c) 5-phenylpentanoyl chloride were used as the starting compounds and treated by the procedures described above to obtain (a') N-(2-phenyl)acetyl—Pro—Pro—OMe (SUAM 1334), (b') N—(3-phenyl)propionyl—Pro—Pro—OMe (SUAM 1337) and (c') N—(5-phenyl)pentanoyl—Pro—Pro—OMe (SUAM 1340), respectively. All of these compounds were oily.

EXAMPLE 2

(a) N—(4-phenyl)butanoyl—Phe—Pro—CH₂OH (SUAM 1233)

N—(4-phenyl)butanoyl—Phe—Pro—OMe (SUAM 1232) (1.3 g) obtained in Example 1 and sodium borohydride (460 mg) were dissolved in tertiary butyl alcohol (20 ml) and heated to 80° C. with stirring. Absolute methanol (3.4 ml) was added dropwise under reflux, and thereafter the mixture was refluxed for 2 hours with stirring. After reaction, the heated mixture was cooled to room temperature and several milliliters of water was added under cooling with ice to inactivate unreacted sodium borohydride. After methanol and tertiary butyl alcohol were distilled off under vacuum, the residue was extracted with ethyl acetate. The extract was washed with brine and dried over anhydrous magnesium sulfate. The solvent was distilled off under vacuum and the resulting residue was purified by column chromatography on silica gel to obtain the end compound as an oil (1.2 g).

In place of N—(4-phenyl)butanoyl—Phe—Pro—OMe, (a) N—(4-phenyl)butanoyl—Met—Pro—OMe, (b) N—(4-phenyl)butanoyl—norLeu—Pro—OMe, (c) N—(4-phenyl)butanoyl—Ala—Pro—OMe, (d) N—(4-phenyl)butanoyl—Val—Pro—OMe and (e) N—(4-phenyl)butanoyl—Leu—Pro—OMe were used as the starting compounds and treated by the procedures described above to obtain (a') N—(4-phenyl)butanoyl—Met—Pro—CH₂OH (SUAM 1344), (b') N—(4-phenyl)butanoyl—norLeu—Pro—CH₂OH (SUAM 1236), (c') N—(4-phenyl)butanoyl—Ala—Pro—CH₂OH (SUAM 1109), (d') N—(4-phenyl)butanoyl—Val—Pro—CH₂OH (SUAM 1116) and (e') N—(4-pehnyl)butanoyl—Leu—Pro—CH₂OH (SUAM 1114), respectively. All of these compounds were oily.

(b) N—(4-phenyl)butanoyl—Pro—Pro—CH₂OH (SUAM 1230)

A mixture of the N—(4-phenyl)butanoyl—Pro—Pro—OMe (SUAM 1229) (1.3 g) obtained in Example 1 and sodium borohydride (510 mg) was dissolved in tertiary butyl alcohol (20 ml) and heated to 80° C. with stirring. Absolute methanol (3.8 ml) was added dropwise under reflux, and thereafter the mixtue was refluxed for 2 hours with stirring. After reaction, the heated mixture was cooled to room temperature and several milliliters of water was added under cooling with ice to inactivate unreacted sodium borohydride. After methanol and tertiary butyl alcohol were distilled off under vacuum, the residue was subjected to extraction with ethyl acetate. The extract was washed with brine and dried over anhydrous magnesium sulfate. The solvent was distilled off under vacuum and the resulting crude product was purified by column chromatography on silica gel to obtain the end compound as an oil (1.2 g).

In place of N—(4-phenyl)butanoyl—Pro—Pro—OMe, (a) N-(2-pehnyl)acetyl—Pro—Pro—OMe, (b) N—(3-phenyl)propionyl—Pro—Pro—OMe and (c) N—(5-pehnyl)pentanoyl—Pro—Pro—OMe were used as the starting compounds and treated by the procedures described above to obtain (a')—N—(2-phenyl(acetyl—Pro—Pro—CH₂OH (SUAM 13359, (b') N—(3-phenyl)propionyl—Pro—Prop—CH₂OH (SUAM 1338) and (c') N—(5-phenyl)pentanoyl—Pro—Pro—CH₂OH (SUAM 1341), respectively. All of these compounds were oily.

EXAMPLE 3

(a) N—(4-phenyl)butanoyl—Phe—Pro—CHO (SUAM 1234)

A mixture of N—(4-phenyl)butanoyl—Phe—Pro—CH₂OH (SUAM 1233) (1.2 g) obtained in Example 2 and TEA (1.6 ml) was dissolved in anhydrous dimethyl sulfoxide (8 ml), and to the stirred solution, a solution of sulfur trioxide-pyridine complex (1.9 g) in dimethyl sulfoxide (8 ml) was added. After stirring the mixture at room temperature for about 20 minutes, the reaction solution was poured into iced water (100 ml) and subjected to extraction with ethyl acetate. The extract was washed successively with 10% aqueous citric acid, brine, saturated aqueous sodium bicarbonate and brine, and dried over anhydrous magnesium sulfate. After distilling off the solvent under vacuum, the resulting crude product was purified by column chromatography on silica gel to obtain the end compound as an oil (800 mg).

In place of N—(4-phenyl)butanoyl—Phe—Pro—CH₂OH, (a) N—(4-phenyl)butanoyl—Met—Pro—CH₂OH, (b) N—(4-phenyl)butanoyl—norLeu—Pro—CH₂OH, (c) N—(4-phenyl)butanoyl—Ala—Pro—CH₂OH, (d) N—(4-phenyl)butanoyl—Val—Pro—CH₂OH and (e) N—(4-phenyl)butanoyl—Leu—CH₂OH were used as the starting compounds and treated by the procedures described above to obtain (a') N—(4-phenyl)butanoyl—Met—Pro—CHO (SUAM 1345), (b') N—(4-phenyl)butanoyl—norLeu—Pro—CHO (SUAM 1333), (c') N—(4-phenyl)butanoyl—Ala—Pro—CHO (SUAM 1110), (d') N—(4-phenyl)butanoyl—Val—Pro—CHO (SUAM 1117) and (e') N—(4-phenyl)butanoyl—Leu—Pro—CHO (SUAM 1115), respectively. All of these compounds were oily.

(b) N—(4-phenyl)butanoyl—Pro—Pro—CHO (SUAM 1231)

A mixture of N—(4-phenyl)butanoyl—Pro—Pro—CH₂OH (SUAM 1230) (1.3 g) obtained in Example 2 and TEA (2.0 ml) was dissolved in anhydrous dimethyl sulfoxide (8 ml), and to the stirred solution, a solution of sulfur trioxide-pyridine complex (2.3 g) in dimethyl sulfoxide (8 ml) was added. After stirring the mixture at a room temperature for about 20 minutes, the reaction solution was poured into iced water (100 ml) and subjected to extraction with ethyl acetate. The extract was washed successively with 10% aqueous citric acid, brine, saturated aqueous sodium bicarbonate and brine, and dried over anhydrous magnesium sulfate. After distilling off the solvent under vacuum, the resulting crude produce was purified by column chromatography on silica gel to obtain the end compound as an oil (700 mg).

In place of N—(4-phenyl)butanoyl—Pro—Pro—CH₂OH, (a) N—(2-phenyl)acetyl—Pro—Pro—CH₂OH (SUAM 1335), (b) N—(3-phenyl)propionyl—Pro—Pro—CH₂OH (SUAM 1338) and (c) N—(5-phenyl)pentanoyl—Pro—Pro—CH₂OH (SUAM 1341) were used as the starting compounds and treated by the procedures described above to obtain (a') N—(2-phenyl)acetyl—Pro—Pro—CHO (SUAM 1336), (b') N—(3-phenyl)propionyl—Pro—Pro—CHO (SUAM 1339) and (c') N—(5-phenyl)pentanoyl—Pro—Pro—CHO (SUAM 1342), respectively. The analytical data for the compounds obtained in Examples 1 to 3 are listed in Table 1.

All the compounds shown in Table 1 are oily and soluble in carbon tetrachloride, ether, chloroform, methylene chloride, ethyl acetate and methanol.

When the effects of these compounds for inhibiting decomposition of Z—glycyl—prolyl—β—naphthylamide by prolyl endopeptidase were examined, they exhibited very high anti-prolyl endopeptidase activities as will be shown in the later-described Example 4, and no inhibitory activity to proteinase such as papain, bromelain, trypsin, chymotrypsin, thermolysin and pepsin.

These compounds obtained in this way are novel and have anti-amnesic effects as shown in Example 5.

TABLE 1

| Example No. | SUAM No. | Property | IR Spectrum (Film, $cm^{-1}$) | Proton NMR Spectrum in $CDCl_3$ δ (ppm) from TMS | $[\alpha]_D$ | EI-MS (m/z) |
|---|---|---|---|---|---|---|
| 1 (a) | 1232 | oily | 3300, 1740, 1630, 1530, 1450, 1190, 1170, 740, 700 | 1.70–2.20(8H,m), 2.54(2H,m), 3.00(2H,m), 3.43–3.67(2H,m), 3.73(3H,s), 4.44(1H,m), 4.96(1H,m), 6.16(1H,d,J = 7.8 Hz), 7.13(5H,s), 7.24(5H,s) | | |
| 1 (a) | 1343 | oily | 3300, 2940, 2920, 2870, 1740, 1620, 1520, 1440, 12 | 1.62–2.29(10H,m), 2.05(3H,s), 2.29–2.72(4H,m), 3.30–3.93 (2H,m), 3.63(3H,s), 4.38(1H,m), 4.94(1H,m), 6.77(H,d,J = 7.8 Hz), 7.14(5H,s) | | |
| 1 (a) | 1235 | oily | 3270, 2960, 2870, 1740, 1660, 1530, 1440, 1190, 1170, 730, 700 | 0.92(3H,m), 1.16–1.60(6H,m), 1.77–2.44(8H,m), 2.64(2H,m), 3.52(2H,m), 3.66(3H,s), 4.47(1H,m), 4.77(1H,m), 7.16(5H,s), 7.50(1H,d,J = 9.0 Hz) | | |
| 1 (a) | 1098 | oily | 3300, 2950, 2870, 1740, 1620, 1530, 1450, 1190, 1170, 740, 700 | 1.35(3H,d,J = 7 Hz), 1.90–2.22(8H,m), 2.62(2H,m), 3.51–3.78(2H,m), 3.66(3H,s), 4.46(1H,m), 4.76(1H,m), 6.85(1H,brd,J = 9 Hz), 7.16(5H,s) | $[\alpha]_D^{28}$ −71.8° (c = 0.17, in $CHCl_3$) | 346 ($M^+$) |
| 1 (a) | 1112 | oily | 3300, 2950, 2870, 1740, 1620, 1530, 1430, 1190, 1170, 750, 690 | 0.94, 1.03(3H each, both d, J = 7 Hz), 1.80–2.37(9H,m), 2.63 (2H,m), 3.53–3.78(2H,m), 3.67 (3H,s), 4.48(1H,m), 4.61(1H,dd, J = 7 Hz, 9 Hz), 6.40(1H,brd, J = 9 Hz), 7.18(5H,s) | $[\alpha]_D^{26}$ −65.0° c = 1.71, in $CHCl_3$ | 374 ($M^+$) |
| 1 (a) | 1113 | oily | 3300, 2950, 2870, 1730, 1620, 1530, 1440, 1190, 1170, 740, 690 | 0.95, 1.10(3H each, both d, J=6Hz), 1.60(3H,m), 1.84–2.20 (8H,m), 2.63(2H,m), 3.55–3.73 (2H,m), 3.68(3H,s), 4.48(1H,m), 4.88(1H,m), 6.27(1H,brd,J = 9 Hz), 7.18(5H,s) | $[\alpha]_D^{26}$ −57.8° (c = 1.56, in $CHCl_3$) | 388 ($M^+$) |
| 1 (b) | 1229 | oily | 2950, 2870, 1740, 1640, 1430, 1320, 1190, 1170, 740, 700 | 1.86–2.36(12H,m), 2.63(2H,m), 3.34–3.88(4H,m), 3.66(3H,s), 4.60(2H,m), 7.18(5H,s) | | |
| 1 (b) | 1334 | oily | 2970, 2940, 2870, 1730, 1630, 1420, 1190, 1170, 740, 690 | 1.71–2.46(8H,m), 3.38–3.93(4H,m), 3.67(3H,s), 3.67(2H,s), 4.57(2H,m), 7.22(5H,s) | | |
| 1 (b) | 1337 | oily | 2970, 2940, 2870, 1730, 1630, 1430, 1190, 1170, 740, 700 | 1.75–2.32(8H,m), 2.41–3.17(4H,m), 3.22–3.96(4H,m), 3.66(3H,s), 4.57(2H,m), 7.18(5H,s) | | |
| 1 (b) | 1340 | oily | 2940, 2870, 1730, 1630, 1420, 1190, 1170, 740, 700 | 1.53–1.85(4H,m), 1.90–2.31(10H,m), 2.43–2.80(2H,m), 3.32–3.94(4H,m), 3.65(3H,s), 4.53(2H,m), 7.14(5H,s) | | |
| 2 (a) | 1233 | oily | 3370, 3280, 2930, 2830, 1620, 1530, 1440, 1040, 740, 690 | 1.50–2.31(8H,m), 2.62(2H,m), 3.02(2H,m), 3.34–3.72(4H,m), 4.14(2H,m), 4.94(1H,m), 6.64(1H,d,J = 7.8 Hz), 7.17(5H,s), 7.23(5H,s) | | |
| 2 (a) | 1344 | oily | 3380, 3280, 2950, 2870, 1610, 1440, 1040, 750, 690 | 1.62–2.31(10H,m), 2.03(3H,s), 2.31–2.87(4H,m), 3.18–3.74(4H,m), 4.06(1H,m), 3.97–5.15(2H,m), 7.13(5H,s) | | |
| 2 (a) | 1236 | oily | 3400, 3280, 2960, 2870, 1650, 1620, 1540, 1450, 1050, 750, 700 | 0.88(3H,m), 1.10–1.62(6H,m), 1.68–2.32(8H,m), 2.62(2H,m), 3.35–3.66(4H,m), 3.98(1H,m), 4.44–4.90(2H,m), 6.88(1H,d,J = 7.8 Hz), 7.18(5H,s) | | |

TABLE 1-continued

| Example No. | SUAM No. | Property | IR Spectrum (Film, am$^{-1}$) | Proton NMR Spectrum in CDCl$_3$ δ (ppm) from TMS | $[\alpha]_D$ | EI-MS (m/z) |
|---|---|---|---|---|---|---|
| 2 (a) | 1109 | oily | 3380, 3300, 2940, 2870, 1620, 1530, 1450, 1050, 740, 690 | 1.34(3H,d,J = 7 Hz), 1.84–2.21(8H,m), 2.63(2H,m), 3.56(4H,m), 4.18(1H,m), 4.49–4.86(2H,m), 6.72(1H,brd, J = 9 Hz), 7.17(5H,s) | $[\alpha]_D^{24}$ −62.0° (c = 0.56, in CHCl$_3$) | 316 (M$^+$) |
| 2 (a) | 1116 | oily | 3380, 3280, 2950, 2860, 1610, 1530, 1440, 1040, 740, 690 | 0.95, 1.00(3H each, both d, J = 7 Hz), 1.75–2.2(9H,m), 2.65 (2H,m),3.58(4H,m), 4.15(1H,m), 4.54(1H,t,J = 4 Hz), 4.61(1H,dd, J = 7 Hz, 9 Hz),6.33(1H,brd, J = 9 Hz), 7.18(5H,s) | $[\alpha]_D^{23}$ −32.4° (c = 1.02, in CHCl$_3$) | 346 (M$^+$) |
| 2 (a) | 1114 | oily | 3380, 3280, 2950, 2860, 1620, 1540, 1440, 1050, 740, 690 | 0.94, 0.98(3H each, both d, J = 6 Hz), 1.56(3H,m), 1.75–2.38(8H,m), 2.63(2H,m), 3.58(4H,m), 4.18(1H,m), 4.48)1H,t,J = 4 Hz), 4.86(1H,m), 6.28 (1H, brd,J = 9 Hz), 7.17(5H,s,) | $[\alpha]_D^{24}$ −33.1° (c=1.59, in CHCl$_3$) | 361 (M$^+$ + 1) |
| 2 (b) | 1230 | oily | 3400 (br), 2940, 2820, 1720, 1620, 1450, 1320, 1235, 1040, 740, 700 | 1.80–2.43(12H,m), 2.67(2H,m), 3.33–3.73(6H,m), 4.10(1H,m), 4.63(1H,m), 5.08(1H,m), 7.18(5H,s) | | |
| 2 (b) | 1335 | oily | 3400, 2960, 2870, 1620, 1430, 1040, 740, 690, | 1.65–2.82(8H,m), 3.31–4.33(7H,m), 3.68(2H,s), 4.49–5.12(2H,m), 7.22(5H,s) | | |
| 2 (b) | 1338 | oily | 3400, 2970, 2870, 1620, 1430, 1050, 740, 690 | 1.66–2.30(8H,m) 2.42–3.13(4H,m), 3.28–4.40(7H,m), 4.46–5.25(2H,m), 7.20(5H,s) | | |
| 2 (b) | 1341 | oily | 3400, 2930, 2870, 1620, 1430, 1050, 740, 690 | 1.48–2.40(14H,m), 2.40–2.78(2H,m), 3.16–4.32(7H,m), 4.35–5.19(2H,m), 7.10(5H,s) | | |
| 3 (a) | 1234 | oily | 3300, 2930, 2870, 2850, 2720, 1730, 1630, 1540, 1440, 1060, 740, 700 | 1.71–2.02(6H,m), 2.15(2H,m), 2.55(2H,m), 3.06(2H,m), 3.28–3.86(2H,m), 4.20(1H,m), 5.02(1H,m), 7.18(5H,s), 7.25(5H,s), 9.19(1H,d,J = 2.0 Hz) | | |
| 3 (a) | 1342 | oily | 3300, 2920, 2880, 2720, 1730, 1620, 1530, 1450, 750, 700 | 1.67–2.32(10H,m), 3.10(3H,s), 2.32–2.83(4H,m), 3.40–3.90(2H,m), 4.03–5.26(2H,m), 7.19(5H,s), 9.38(1H,d,J = 2.0 Hz) | | |
| 3 (a) | 1333 | oily | 3300 ,2960, 2870, 2730, 1730, 1620, 1540, 1440, 740, 700 | 0.88(3H,m) 1.10–1.60(6H,m), 1.68–2.38(8H,m), 2.13(2H,m), 3.25–3.82(2H,m), 4.53–4.98 (2H,m), 6.86(1H,d,J = 7.8 Hz), 7.16(5H,s), 8.35(1H,d,J = 2.0 Hz | | |
| 3 (a) | 1110 | oily | 3300, 2970, 2870, 2720, 1720, 1620, 1530, 1450, 740, 690 | 1.40(3H,d,J = 6 Hz), 1.88–2.28 (8H,m), 2.65(2H,m), 3.56–3.80 (2H,m), 4.52(1H,m), 4.78(1H,m), 6.35(1H,brd,J = 9 hz), 7.21(5H,s), 9.49(1H,d,J = Hz) | $[\alpha]_D^{24}$ −62.0° (c = 0.56, in CHCl$_3$) | 316 (M$^+$) |
| 3 (a) | 1117 | oily | 3300, 2960, 2870, 2720, 1730, 1620, 1530, 1440, 740, 690, | 0.95, 1.02(3H each, both d, J = 7 Hz), 1.82–2.27(9H,m), 2.61 (2H,m), 3.52–3.83(2H,m), 4.44 (1H,m), 4.62(1H,dd,J = 7 Hz,9 Hz, 6.63(1H, brd,J = 9 Hz), 7.18(5H,s), 9.46(1H,d,J = 1.5 Hz) | $[\alpha]_D^{31}$ −65.0° (c = 1.00, in CHCl$_3$) | 345 (M$^+$ + 1) |
| 3 (a) | 1115 | oily | 3280, 2950, 2860, 2720, 1720, 1620, 1530, 1450, 740, 690, | 0.95, 1.01(3H each, both d, J = 6 Hz), 1.57(3H,m), 1.85–2.41 (8H,m), 2.62(2H,m),3.45–3,83 (2H,m), 4.48(1H,m), 4.82(1H,m), 6.40(1H,brd,J = 9 Hz), 7.18(5H,s), 9.45(1H,d,J = 2 Hz) | $[\alpha]_D^{31}$ −44.2° (c = 0.33, in CHCl$_3$) | 358 (M$^+$) |
| 3 (b) | 1231 | oily | 2970, 2870, 1730, 1630, 1440, 1320, 2720, 740, 700 | 1.88–2.43(12H,m), 2.63(2H,m), 3.28–3.82(4H,m), 4.57(2H,m), 7.13(5H,s), 9.49(1H,d,J = 1.0 Hz) | | |
| 3 (b) | 1336 | oily | 2970, 2880, 1720, 1640, 1420, 740 690 | 1.72–2.43(8H,m), 3.27–3.95(4H,m), 3.67(2H,s), 4.63(2H,m), 7.22(5H,s), 9.42(1H,d,J = 1.0 Hz) | | |
| | | | 2970, 2870, 2800, 2700, | 1.66–2.32(8H,m), 2.42–3.13(4H,m), | | |

TABLE 1-continued

| Example No. | SUAM No. | Property | IR Spectrum (Film, am$^{-1}$) | Proton NMR Spectrum in CDCl$_3$ δ (ppm) from TMS | $[\alpha]_D$ | EI-MS (m/z) |
|---|---|---|---|---|---|---|
| 3 (b) | 1339 | oily | 1720, 1630, 1430, 740, 690 | 3.30–3.98(4H,m), 4.53(2H,m), 7.19(5H,s), 9.43(1Hd,d,J = 1.0 Hz) | | |
| | | | 2970, 2880, 2800, 2710 | 1.51–2.46(14H,m), 2.46–2.83(2H,m), | | |
| 3 (b) | 1342 | oily | 1720, 1640, 1430, 740, 700 | 3.20–3.92(4H,m) 4.52(2H,m), 7.14(5H,s), 9.39(1H,d,J = 2.0 Hz) | | |

EXAMPLE 4

Measurement of Anti-prolyl Endopeptidase Activity

The method of Yoshimoto and Tsuru (T. Yoshimoto and D. Tsuru, Agr. Biol. Chem. 42, 2417, 1978) was used to measure the anti-prolyl endopeptidase activities of several compounds according to the present invention. A mixture of 0.0025M Z—glycyl—proline—β—naphthylamide (0.25 ml), 0.1M phosphate buffer (pH 7.0; 0.99 ml) and a solution of a particular anti-prolyl endopeptidase compound (0.01 ml) was incubated in a test tube at 37° C. for 3 minutes. Thereafter 0.1 m of a solution of prolyl endopeptidase (0.2 U/ml) was added and the mixture was heated at 35° C. for 10 minutes. After the reaction, 2.0 ml of Triton x-100 in 1M acetate buffer (pH 4.0) was added to the reaction mixture until the final concentration of the surfactant was 10%. The mixture was left at a room temperature for 15 minutes and the absorbance (a) at 410 nm was measured.

A sample for a blind test was prepared by using the buffer solely in place of the anti-prolyl endopeptidase compound and its absorbance (b) was also measured. The percent inhibition of prolyl endopeptidase was calculated by the formula: $[(b-a)/b] \times 100$, and the amount of a specific compound needed to achieve 50% inhibition (IC$_{50}$) was determined. The results are shown in Table 2.

TABLE 2

| Compound | IC$_{50}$ (ng/test tube) |
|---|---|
| SUAM 1231 | 0.2 |
| SUAM 1234 | 0.3 |
| SUAM 1333 | 0.4 |
| SUAM 1345 | 0.7 |
| SUAM 1336 | 1.0 |
| SUAM 1339 | 0.4 |
| SUAM 1342 | 0.2 |
| SUAM 1115 | 0.3 |
| SUAM 1117 | 0.2 |

EXAMPLE 5

Measurement of Preventive Effect against Experimental Amnesia caused in Rats by Scopolamine (Intraperitoneal Administration)

Several of the anti-prolyl endopeptidase compounds according to the present invention were checked for their ability to prevent the inhibition of long-term memory fixation by scopolamine. Solutions of physiological saline which contained 20 μg/kg of selected compounds of the present invention were administered intraperitoneally once a day to Wister male rats (100 to 120 g). One hour after the administration, electric shocks were applied to the rats so that they would acquire passive avoidance learning. Immediately thereafter, scopolamine was administered intraperitoneally to each rat in an amount of 3 mg per kg of body weight.

The results of the test were assessed both 24 hours and 48 hours after the administration of scopolamine. The number of amnesic rats and of sound rats was counted for each of the control group (rats to which the test compounds were not administered but to which only scopolamine and physiological saline were administered intraperitoneally) and the treated group (rats to which both the test compound and scopolamine were administered). The results are shown in Table 3. With respect to SUAMs 1110, 1115 and 1117, administration of 1 mg/kg did not manifest the desired effect but when 0.1 mg/kg and 0.025 mg/kg of each was administered, very strong effects were produced. SUAMs 1231 and 1333 also exhibited a strong effect at 0.020 mg/kg. Thus these compounds exhibited very strong anti-amnesic effects in a low dose without producing any apparent change in the rats when the dose was raised up to more than 100 mg/kg.

TABLE 3

| | | | Amnesia test with rats (intraperitoneal administration) | | | | | | |
|---|---|---|---|---|---|---|---|---|---|
| | | | | Learning | | | | Pharmacological effects | |
| | | | | Initial avoidance time (sec.) | No. of avoidances during learning | Learning time (sec.) | Avoidance time (sec.) | | |
| | Sample | Drug administered after learning | No. of rats tested | | | | After 24 hrs. | After 48 hrs. | No. of amnesic rats/No. of rats tested | Percentage amnesia |
| 1 | physiological saline | physiological saline | 9 | 6.2 | 2.3 | 100 | 230.0 | 209.3 | 3/9 | 33 |
| 2 | physiological saline | scopolamine (3 mg/kg, i.p.) | 10 | 2.7 | 2.9 | 100 | 90.6 | 110.4 | 8/10 | 80 |
| 3 | SUAM 1110 (1 mg/kg, i.p.) | scopolamine (3 mg/kg, i.p.) | 10 | 3.8 | 1.6 | 100 | 272.8 | 271.2 | 1/10 | 10 |
| 4 | SUAM 1110 (250 μg/kg, i.p.) | scopolamine (3 mg/kg, i.p.) | 10 | 5.2 | 3.0 | 100 | 300.0 | 300.0 | 0/10 | 0 |
| 5 | SUAM 1117 (1 mg/kg, i.p.) | scopolamine (3 mg/kg, i.p.) | 10 | 3.8 | 2.2 | 100 | 161.6 | 125.0 | 6/10 | 60 |

TABLE 3-continued

Amnesia test with rats (intraperitoneal administration)

| | Sample | Drug administered after learning | No. of rats tested | Learning | | | Avoidance time (sec.) | | Pharmacological effects | |
|---|---|---|---|---|---|---|---|---|---|---|
| | | | | Initial avoidance time (sec.) | No. of avoidances during learning | Learning time (sec.) | After 24 hrs. | After 48 hrs. | No. of amnesic rats/No. of rats tested | Percentage amnesia |
| 6 | SUAM 1117 (250 μg/kg, i.p.) | scopolamine (3 mg/kg, i.p.) | 10 | 2.4 | 2.4 | 100 | 232.0 | 194.4 | 4/10 | 40 |
| 7 | SUAM 1117 (100 μg/kg, i.p.) | scopolamine (3 mg/kg, i.p.) | 10 | 3.2 | 3.2 | 100 | 300.0 | 300.0 | 0/10 | 0 |
| 8 | SUAM 1117 (25 μg/kg, i.p.) | scopolamine (3 mg/kg, i.p.) | 10 | 1.9 | 2.2 | 100 | 300.0 | 289.5 | 1/10 | 10 |
| 9 | SUAM 1115 (250 μg/kg, i.p.) | scopolamine (3 mg/kg, i.p.) | 10 | 1.5 | 3.0 | 100 | 193.2 | 217.1 | 3/10 | 30 |
| 10 | SUAM 1115 (100 μg/kg, i.p.) | scopolamine (3 mg/kg, i.p.) | 10 | 2.5 | 3.0 | 100 | 300.0 | 300.0 | 0/10 | 0 |
| 11 | SUAM 1115 (25 μg/kg, i.p.) | scopolamine (3 mg/kg, i.p.) | 10 | 2.7 | 2.4 | 100 | 300.0 | 300.0 | 0/10 | 0 |
| 12 | SUAM 1231 (20 μg/kg, i.p.) | scopolamine (3 mg/kg, i.p.) | 10 | 3.1 | 2.4 | 100 | 300.0 | — | 0/10 | 0 |
| 13 | SUAM 1333 (20 μg/kg, i.p.) | scopolamine (3 mg/kg, i.p.) | 10 | 1.7 | 2.3 | 100 | 300.0 | — | 0/10 | 0 |

EXAMPLE 6

Anti-hypoxia effect

Male mice of ddY-strain weighing 25 to 34 g were allotted to groups consisting of 7 to 10 animals each. Each compound to be tested was suspended in physiological saline with 2 to 3 drops of Tween 80® added thereto, and administered intraperitoneally at the rate of 0.1 ml per 10 g of body weight.

Each mouse was put into a 1 l desiccator 30 minutes after the administration, and the pressure in the desiccator was reduced to 180 mmHg by means of a vacuum pump. The period from the start of pressure reduction to the respiratory arrest of the mouse was assumed to be the survival time (minute) of the mouse.

If the mouse survived more than 15 minutes, its survival time was recorded as being 15 minutes. A student's t-test was adopted for the significance analysis.

The results are shown in Table 4.

EXAMPLE 7

Acute Toxicity Test in Mice

The compounds of the present invention were checked for their acute toxicity in CDF-1 strain male mice (body weight: 27.2 to 30.1 g) purchased from Awazu Laboratory Animals Co., Ltd.

Test samples were prepared by dissolving the respective compounds in DMSO, and a portion (0.1 ml) of the so conditioned test sample was administered intraperitoneally to each of the mice used. Each of the treated groups consisted of five mice. After 24 hours and 48 hours had passed from the time of administration, respectively, the mice were observed. The average amount of each test compound administered in this Example is shown in Table 5.

TABLE 5

| Compound No. | Average-Dose (mg/kg) |
|---|---|
| No. 1 SUAM 1231 | 634.6 |
| No. 2 SUAM 1333 | 707.7 |

Each of the groups tested remained sound and showed no sign of intoxication at the times of observation 24 hours and 48 hours after the administration of the doses shown in Table 5.

The present invention includes pharmaceutical compositions which contain compounds according to the present invention which are effective for the improvement of symptoms caused by organic disorders of the brain together with adjuvants which are acceptable from the pharmaceutical point of view.

These active ingredients and pharmaceutical compositions are administered orally in suitable solid forms such as capsules, tablets and powders, or liquid forms such as elixir, syrup and suspensions. They may also be administered parenterally, e.g., in the form of injection or suppository.

As an example of suitable excipients for solid drugs which are contained in drug components, a carrier in solid powder form may be cited such as lactose, saccharose, mannitol, sorbitol, cellulose and glycine.

As an example of suitable lubricants, silicon dioxide, talc, magnesium stearate and polyethylene glycol may be cited, while starch, gelatin, tragacanth, methyl cellulose, sodium carboxymethyl cellulose and polyvinyl

TABLE 4

| Drug | Chemical structure | Dose (mg/kg i.p.) | No. of survival/used | | Survival time (min., Mean ± S.E.) | | Ratio |
|---|---|---|---|---|---|---|---|
| | | | Control | Drug | Control | Drug | |
| SUAM-1234 | (structure shown) | 1 | 0/10 | 0/7 | 2.32 ± 0.11 | 2.88 ± 0.17* | 1.24 |
| | | 10 | 0/10 | 0/7 | 2.25 ± 0.15 | 2.45 ± 0.19 | 1.09 |

*$P < 0.05$ pyrrolidone may be cited as binders. Starch or agar may be used as a disintegrator.

The compounds according to the present invention are orally administered in a daily dose of 10 to 4,000 mg, preferably, 100 to 1,000 mg per adult. Alternatively, they may be administered parenterally in a dose of 1 to 2,000 mg, preferably, 50 to 500 mg. It is understood that the dosage will differ depending upon the symptoms of the disease, the age and weight of a patient, the stage of the symptoms and the form of administration.

| Formulation 1 | |
| --- | --- |
| active substance | 10 parts |
| lactose | 75 parts |
| heavy magnesium oxide | 15 parts |

These components were uniformly mixed and formed into tablets or capsules.

| Formulation 2 | |
| --- | --- |
| active substance | 45 parts |
| starch | 15 parts |
| lactose | 40 parts |

These components were uniformly mixed and formed into powders or granules.

| Formulation 3 | |
| --- | --- |
| active substance | 1 part |
| surfactant | 5 parts |
| physiological saline | 94 parts |

These components were mixed under warming and were sterilized to obtain injections.

As described above, the compounds according to the present invention exhibit appreciable anti-polyl endopeptidase activity and anti-amnesic effects. The acute toxicity test results show that the compounds cause no toxicity even when administered in such high doses as about 500 mg/kg/mouse. Because of this relatively wide margin of safety, as compared with their remarkable anti-prolyl endopeptidase activity, the compounds of the present invention hold promise as pharmaceuticals for preventing and curing amnesia.

What is claimed is:

1. A compound which is expressed by the formula:

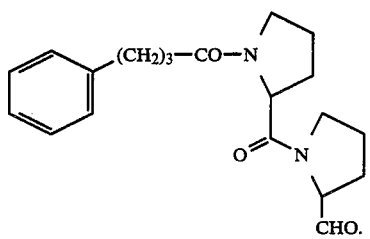

2. An anti-amnesic agent comprising a pharmaceutically effective amount of a compound of the formula:

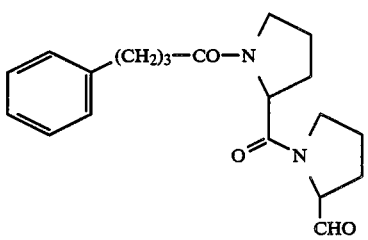

together with a pharmaceutically acceptable carrier.

* * * * *

UNITED STATES PATENT AND TRADEMARK OFFICE
CERTIFICATE OF CORRECTION

PATENT NO. : 4,873,342

DATED : October 10, 1989

INVENTOR(S) : Tanaka et al.

It is certified that error appears in the above-identified patent and that said Letters Patent is hereby corrected as shown below:

In the Abstract, change "depeptide" to --dipeptide--.

Col. 1, line 20, change "cuased" to --caused--;

line 61, change "vasolidators" to --vasodilators--.

Col. 4, 1st formula change

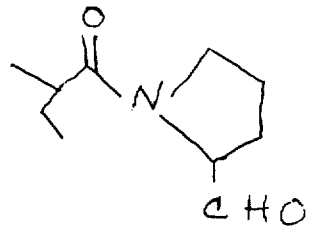

to

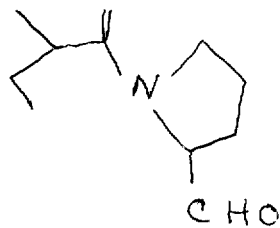

Col. 7, line 15, change "trioxide-pyridine complex" to --trioxide-pyridine--.

UNITED STATES PATENT AND TRADEMARK OFFICE
CERTIFICATE OF CORRECTION

PATENT NO. : 4,873,342

DATED : October 10, 1989

INVENTOR(S) : Tanaka, et al

It is certified that error appears in the above-identified patent and that said Letters Patent is hereby corrected as shown below:

Col. 19, line 38, change "anti-polyl" to --anti-prolyl--.

Signed and Sealed this

Eighteenth Day of December, 1990

Attest:

Attesting Officer

HARRY F. MANBECK, JR.

Commissioner of Patents and Trademarks